United States Patent
Tsukui et al.

(10) Patent No.: US 11,104,727 B2
(45) Date of Patent: Aug. 31, 2021

(54) ANTI-CANINE TARC ANTIBODY USED FOR TREATMENT AND DIAGNOSIS OF CANINE ATOPIC DERMATITIS

(71) Applicant: NIPPON ZENYAKU KOGYO CO., LTD., Koriyama (JP)

(72) Inventors: Toshihiro Tsukui, Koriyama (JP); Miyuki Kageyama, Koriyama (JP); Masahiro Kato, Koriyama (JP); Rieko Suzuki, Koriyama (JP)

(73) Assignee: NIPPON ZENYAKU KOGYO CO., LTD., Koriyama (JP)

( * ) Notice: Subject to any disclaimer, the term of this patent is extended or adjusted under 35 U.S.C. 154(b) by 494 days.

(21) Appl. No.: 15/768,183

(22) PCT Filed: Oct. 13, 2016

(86) PCT No.: PCT/JP2016/080339
§ 371 (c)(1),
(2) Date: Apr. 13, 2018

(87) PCT Pub. No.: WO2017/065203
PCT Pub. Date: Apr. 20, 2017

(65) Prior Publication Data
US 2018/0319879 A1 Nov. 8, 2018

(30) Foreign Application Priority Data
Oct. 14, 2015 (JP) .............................. JP2015-203123

(51) Int. Cl.
| | | |
|---|---|---|
| *C07K 16/24* | (2006.01) | |
| *G01N 33/53* | (2006.01) | |
| *A61P 37/06* | (2006.01) | |
| *G01N 33/577* | (2006.01) | |
| *A61K 39/00* | (2006.01) | |
| *C12N 5/10* | (2006.01) | |
| *A61P 17/00* | (2006.01) | |
| *C12N 15/09* | (2006.01) | |
| *C12N 15/85* | (2006.01) | |

(52) U.S. Cl.
CPC .............. *C07K 16/24* (2013.01); *A61P 17/00* (2018.01); *A61P 37/06* (2018.01); *C12N 5/10* (2013.01); *C12N 15/09* (2013.01); *C12N 15/8509* (2013.01); *G01N 33/53* (2013.01); *G01N 33/577* (2013.01); *A61K 2039/552* (2013.01); *C07K 2317/24* (2013.01); *C07K 2317/55* (2013.01); *C07K 2317/565* (2013.01); *C07K 2317/569* (2013.01); *C12N 2015/8518* (2013.01)

(58) Field of Classification Search
None
See application file for complete search history.

(56) References Cited

U.S. PATENT DOCUMENTS

| | | |
|---|---|---|
| 5,932,703 A | 8/1999 | Godiska et al. |
| 6,548,631 B1 | 4/2003 | DeVico et al. |
| 2004/0077047 A1 | 4/2004 | Kuck et al. |
| 2013/0171152 A1 | 7/2013 | Spriggs et al. |

FOREIGN PATENT DOCUMENTS

| | | |
|---|---|---|
| EP | 1 221 618 A1 | 7/2002 |
| JP | 10-507646 A | 7/1998 |
| JP | 2001-520002 A | 10/2001 |
| JP | 2005-6583 A | 1/2005 |
| JP | 2005-104936 A | 4/2005 |
| JP | 2015-25006 A | 2/2015 |
| WO | WO 02/053758 A2 | 7/2002 |

OTHER PUBLICATIONS

International Search Report, issued in PCT/JP2016/080339, dated Jan. 10, 2017.
Maeda et al., "Molecular Cloning of Canine Thymus and Activation-Regulated Chemokine (TARC) Gene and Its Expression in Various Tissues", J. Vet. Med. Sci., 2001, vol. 63, No. 9, pp. 1035-1038.
Maeda et al., "Production of a monoclonal antibody to canine thymus and activation-regulated chemokine (TARC) and detection of TARC in lesional skin from dogs with atopic dermatitis", Elsevier. Veterinary Immunology and Immunopathology, 2005, vol. 103, pp. 83-92.
Uchida et al., "Preferential expression of $T_h2$-type chemokine and its receptor in atopic dermatitis", International Immunology, 2002, vol. 14, No. 12, pp. 1431-1438.
Vestergaard et al., "A $Th_2$ Chemokine, TARC, Produced by Keratinocytes May Recruit CLA⁺CCR4⁺ ymphocytes into Lesional Atopic Dermatitis Skin", J. Invest. Dermatol., 2000, vol. 115, No. 4, pp. 640-646.
Written Opinion of the International Searching Authority, issued in PCT/JP2016/080339, dated Jan. 10, 2017.

*Primary Examiner* — Gary B Nickol
*Assistant Examiner* — Jegatheesan Seharaseyon
(74) *Attorney, Agent, or Firm* — Birch, Stewart, Kolasch & Birch, LLP

(57) ABSTRACT

Provided are an anti-canine TARC antibody for use in the treatment and diagnosis of canine atopic dermatitis, and a method for treating or diagnosing canine atopic dermatitis using the same.
An anti-canine TARC monoclonal antibody binding to canine TARC, comprising a heavy chain variable region consisting of the amino acid sequence shown in SEQ ID NO: 2 and a light chain variable region consisting of the amino acid sequence shown in SEQ ID NO: 4, or a functional fragment thereof binding to canine TARC.

6 Claims, 5 Drawing Sheets

Specification includes a Sequence Listing.

Fig. 4

| Primer name | Sequence (5'-3') | | Direction | Target gene to amplify |
|---|---|---|---|---|
| 1 | GCCTCCACCACGGCCCC | (SEQ ID NO:10) | F | IgG-C |
| 2 | GCCGCGGCCGCTCATTTACCCGGAGAATGGG | (SEQ ID NO:11) | R | |
| 3 | AATGATGCCCAGCCAGCCGT | (SEQ ID NO:12) | F | IgG-kappa |
| 4 | GGCACGCGTTTAGTCCACTCTCTGACACT | (SEQ ID NO:13) | R | |
| 5 | GCCGTCGACATGGGGAAGTGTGCAGCCAT | (SEQ ID NO:14) | F | CT1-mouseVH |
| 6 | GGTGGAGGCTGCAGAGACAGTGACCAGAG | (SEQ ID NO:15) | R | |
| 7 | GCCCTCGAGATGGGGACTCAAGACTTTTTG | (SEQ ID NO:16) | F | CT1-mouseVL |
| 8 | GGCATCATTCCGTTTCAGCTCCAGCTTGG | (SEQ ID NO:17) | R | |

(1) Mouse ascites-derived CT-1
(2) Recombinant chimeric CT-1
(3) Negative control (medium)

SEQUENCE LISTING

```
<160> NUMBER OF SEQ ID NOS: 33

<210> SEQ ID NO 1
<211> LENGTH: 441
<212> TYPE: DNA
<213> ORGANISM: Mus musculus
<220> FEATURE:
<221> NAME/KEY: CDS
<222> LOCATION: (1)..(441)

<400> SEQUENCE: 1 atg ggg aag tgt gca gcc atg ggc agg ctt act tct tca ttc ttg cta      48
Met Gly Lys Cys Ala Ala Met Gly Arg Leu Thr Ser Ser Phe Leu Leu
1               5                   10                  15 ctg att gtc cct gca tat gtc ctg tcc cag gtt act ctg aaa gag tct      96
Leu Ile Val Pro Ala Tyr Val Leu Ser Gln Val Thr Leu Lys Glu Ser
            20                  25                  30 ggc cct ggg ata ttg cag ccc tcc cag acc ctc agt ctg act tgt tct     144
Gly Pro Gly Ile Leu Gln Pro Ser Gln Thr Leu Ser Leu Thr Cys Ser
        35                  40                  45 ttc tct ggg ttt tca ctg aac act tct ggt atg ggt gta ggc tgg att     192
Phe Ser Gly Phe Ser Leu Asn Thr Ser Gly Met Gly Val Gly Trp Ile
    50                  55                  60 cgt cag cct tca ggg aag ggt ctg gag tgg ctg gca cac att tgg tgg     240
Arg Gln Pro Ser Gly Lys Gly Leu Glu Trp Leu Ala His Ile Trp Trp
65                  70                  75                  80 gat gat gac aag cgc tat aac cca gcc ctg aag agc cga ctg aca atc     288
Asp Asp Asp Lys Arg Tyr Asn Pro Ala Leu Lys Ser Arg Leu Thr Ile
                85                  90                  95 tcc aag gat acc ttc aac aac cag gta ttc ctc aac atc gcc agt gtg     336
Ser Lys Asp Thr Phe Asn Asn Gln Val Phe Leu Asn Ile Ala Ser Val
            100                 105                 110 gac act gca gat act gcc aca tac tac tgt gct cga ata tac ttc ggt     384
Asp Thr Ala Asp Thr Ala Thr Tyr Tyr Cys Ala Arg Ile Tyr Phe Gly
        115                 120                 125 agt agc ctc gcc tgg ttt gct tac tgg ggc caa ggg act ctg gtc act     432
Ser Ser Leu Ala Trp Phe Ala Tyr Trp Gly Gln Gly Thr Leu Val Thr
    130                 135                 140 gtc tct gca                                                          441
Val Ser Ala
145

<210> SEQ ID NO 2
<211> LENGTH: 147
<212> TYPE: PRT
<213> ORGANISM: Mus musculus
```

<400> SEQUENCE: 2

```
Met Gly Lys Cys Ala Ala Met Gly Arg Leu Thr Ser Ser Phe Leu Leu
1               5                   10                  15

Leu Ile Val Pro Ala Tyr Val Leu Ser Gln Val Thr Leu Lys Glu Ser
            20                  25                  30

Gly Pro Gly Ile Leu Gln Pro Ser Gln Thr Leu Ser Leu Thr Cys Ser
        35                  40                  45

Phe Ser Gly Phe Ser Leu Asn Thr Ser Gly Met Gly Val Gly Trp Ile
    50                  55                  60

Arg Gln Pro Ser Gly Lys Gly Leu Glu Trp Leu Ala His Ile Trp Trp
65                  70                  75                  80

Asp Asp Asp Lys Arg Tyr Asn Pro Ala Leu Lys Ser Arg Leu Thr Ile
                85                  90                  95

Ser Lys Asp Thr Phe Asn Asn Gln Val Phe Leu Asn Ile Ala Ser Val
            100                 105                 110

Asp Thr Ala Asp Thr Ala Thr Tyr Tyr Cys Ala Arg Ile Tyr Phe Gly
        115                 120                 125

Ser Ser Leu Ala Trp Phe Ala Tyr Trp Gly Gln Gly Thr Leu Val Thr
    130                 135                 140

Val Ser Ala
145
```

```
<210> SEQ ID NO 3
<211> LENGTH: 432
<212> TYPE: DNA
<213> ORGANISM: Mus musculus
<220> FEATURE:
<221> NAME/KEY: CDS
<222> LOCATION: (1)..(432)
```

<400> SEQUENCE: 3

```
atg ggg act caa gac ttt ttg tat caa gtt ctc aga atg agg tgc cta      48
Met Gly Thr Gln Asp Phe Leu Tyr Gln Val Leu Arg Met Arg Cys Leu
1               5                   10                  15 gct gag ttc ctg ggg ctg ctt gtg ctc tgg atc cct gga gcc att ggg      96
Ala Glu Phe Leu Gly Leu Leu Val Leu Trp Ile Pro Gly Ala Ile Gly
            20                  25                  30 gat att gtg atg act cag gct aca tcc tct gta ttt gtc act cct gga     144
Asp Ile Val Met Thr Gln Ala Thr Ser Ser Val Phe Val Thr Pro Gly
        35                  40                  45 gat tca gta tcc atc tcc tgc agg tct agt aag agt ctc ctg cat agt     192
Asp Ser Val Ser Ile Ser Cys Arg Ser Ser Lys Ser Leu Leu His Ser
    50                  55                  60 aat ggc aac act tac ttg tat tgg ttc ctg cag agg cca ggc cag tct     240
Asn Gly Asn Thr Tyr Leu Tyr Trp Phe Leu Gln Arg Pro Gly Gln Ser
65                  70                  75                  80 cct cag ctc ctg ata tat cgg atg tcc aac ctt gcc tca gga gtc cca     288
Pro Gln Leu Leu Ile Tyr Arg Met Ser Asn Leu Ala Ser Gly Val Pro
                85                  90                  95 gac agg ttc agt ggc agt ggg tca gga act gct ttc aca ctg aga atc     336
Asp Arg Phe Ser Gly Ser Gly Ser Gly Thr Ala Phe Thr Leu Arg Ile
            100                 105                 110 agt aga gtg gag gct gag gat gtg ggt gtt tat tac tgt atg caa cat     384
Ser Arg Val Glu Ala Glu Asp Val Gly Val Tyr Tyr Cys Met Gln His
        115                 120                 125 cta gaa aat ccc acg ttc ggt gct ggg acc aag ctg gag ctg aaa cgg     432
Leu Glu Asn Pro Thr Phe Gly Ala Gly Thr Lys Leu Glu Leu Lys Arg
    130                 135                 140
```

```
<210> SEQ ID NO 4
<211> LENGTH: 144
<212> TYPE: PRT
<213> ORGANISM: Mus musculus

<400> SEQUENCE: 4

Met Gly Thr Gln Asp Phe Leu Tyr Gln Val Leu Arg Met Arg Cys Leu
1               5                   10                  15

Ala Glu Phe Leu Gly Leu Leu Val Leu Trp Ile Pro Gly Ala Ile Gly
            20                  25                  30

Asp Ile Val Met Thr Gln Ala Thr Ser Ser Val Phe Val Thr Pro Gly
        35                  40                  45

Asp Ser Val Ser Ile Ser Cys Arg Ser Ser Lys Ser Leu Leu His Ser
    50                  55                  60

Asn Gly Asn Thr Tyr Leu Tyr Trp Phe Leu Gln Arg Pro Gly Gln Ser
65                  70                  75                  80

Pro Gln Leu Leu Ile Tyr Arg Met Ser Asn Leu Ala Ser Gly Val Pro
                85                  90                  95

Asp Arg Phe Ser Gly Ser Gly Ser Gly Thr Ala Phe Thr Leu Arg Ile
            100                 105                 110

Ser Arg Val Glu Ala Glu Asp Val Gly Val Tyr Tyr Cys Met Gln His
        115                 120                 125

Leu Glu Asn Pro Thr Phe Gly Ala Gly Thr Lys Leu Glu Leu Lys Arg
    130                 135                 140

<210> SEQ ID NO 5
<211> LENGTH: 12
<212> TYPE: DNA
<213> ORGANISM: Artificial
<220> FEATURE:
<223> OTHER INFORMATION: Primer

<400> SEQUENCE: 5
tccakagttc ca                                                            12

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
gggaartarc ccttgaccag gca                                                23

<210> SEQ ID NO 7
<211> LENGTH: 23
<212> TYPE: DNA
<213> ORGANISM: Artificial
<220> FEATURE:
<223> OTHER INFORMATION: Primer

<400> SEQUENCE: 7
gggaartagc ctttgacaag gca                                                23

<210> SEQ ID NO 8
<211> LENGTH: 12
<212> TYPE: DNA
<213> ORGANISM: Artificial
<220> FEATURE:
<223> OTHER INFORMATION: Primer
```

```
<400> SEQUENCE: 8
gctgtcctga tc                                                    12

<210> SEQ ID NO 9
<211> LENGTH: 26
<212> TYPE: DNA
<213> ORGANISM: Artificial
<220> FEATURE:
<223> OTHER INFORMATION: Primer

<400> SEQUENCE: 9
cactgccatc aatcttccac ttgaca                                     26

<210> SEQ ID NO 10
<211> LENGTH: 17
<212> TYPE: DNA
<213> ORGANISM: Artificial
<220> FEATURE:
<223> OTHER INFORMATION: Primer

<400> SEQUENCE: 10
gcctccacca cggcccc                                               17

<210> SEQ ID NO 11
<211> LENGTH: 31
<212> TYPE: DNA
<213> ORGANISM: Artificial
<220> FEATURE:
<223> OTHER INFORMATION: Primer

<400> SEQUENCE: 11
gccgcggccg ctcatttacc cggagaatgg g                               31

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
aatgatgccc agccagccgt                                            20

<210> SEQ ID NO 13
<211> LENGTH: 29
<212> TYPE: DNA
<213> ORGANISM: Artificial
<220> FEATURE:
<223> OTHER INFORMATION: Primer

<400> SEQUENCE: 13
ggcacgcgtt tagtccactc tctgacact                                  29

<210> SEQ ID NO 14
<211> LENGTH: 29
<212> TYPE: DNA
<213> ORGANISM: Artificial
<220> FEATURE:
<223> OTHER INFORMATION: Primer

<400> SEQUENCE: 14
gccgtcgaca tggggaagtg tgcagccat                                  29
```

<210> SEQ ID NO 15
<211> LENGTH: 29
<212> TYPE: DNA
<213> ORGANISM: Artificial
<220> FEATURE:
<223> OTHER INFORMATION: Primer

<400> SEQUENCE: 15
ggtggaggct gcagagacag tgaccagag                                29

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
gccctcgaga tggggactca agactttttg                              30

<210> SEQ ID NO 17
<211> LENGTH: 29
<212> TYPE: DNA
<213> ORGANISM: Artificial
<220> FEATURE:
<223> OTHER INFORMATION: Primer

<400> SEQUENCE: 17
ggcatcattc cgtttcagct ccagcttgg                               29

<210> SEQ ID NO 18
<211> LENGTH: 426
<212> TYPE: DNA
<213> ORGANISM: Mus musculus

<400> SEQUENCE: 18
atgggatgga tctgtatcat ctttcttgtg gcaacagcta caggtgtcca ctcccaggtc     60
aagctgctgc agtctggggc tgcactggtg aagcctggag cctctgtgaa gatgtcttgc    120
aaagcttctg cttattcatt cactgactac tgggtgagct gggtgaagca gagtcatgga    180
aagagccttg agtggattgg ggaaatttat cctaacagtg gtgctactaa cttcaatgaa    240
aagttcaagg gcaaggccac attgactgta gacaaatcca ccagcacagc ctatatggag    300
ctcagcagat tgacatctga ggactctgca atctattact gtacaagagg ggttggttat    360
tactacagtg gtgacgactg gtactttgac ttctggggcc aggaaccat ggtcaccgtg    420 tcctca                                                               426

<210> SEQ ID NO 19
<211> LENGTH: 142
<212> TYPE: PRT
<213> ORGANISM: Mus musculus

<400> SEQUENCE: 19

Met Gly Trp Ile Cys Ile Ile Phe Leu Val Ala Thr Ala Thr Gly Val
1               5                   10                  15

His Ser Gln Val Lys Leu Leu Gln Ser Gly Ala Ala Leu Val Lys Pro
            20                  25                  30

Gly Ala Ser Val Lys Met Ser Cys Lys Ala Ser Ala Tyr Ser Phe Thr
        35                  40                  45

Asp Tyr Trp Val Ser Trp Val Lys Gln Ser His Gly Lys Ser Leu Glu
    50                  55                  60

```
Trp Ile Gly Glu Ile Tyr Pro Asn Ser Gly Thr Asn Phe Asn Glu
 65                  70                  75                  80

Lys Phe Lys Gly Lys Ala Thr Leu Thr Val Asp Lys Ser Thr Ser Thr
                 85                  90                  95

Ala Tyr Met Glu Leu Ser Arg Leu Thr Ser Glu Asp Ser Ala Ile Tyr
            100                 105                 110

Tyr Cys Thr Arg Gly Val Gly Tyr Tyr Ser Gly Asp Asp Trp Tyr
        115                 120                 125

Phe Asp Phe Trp Gly Pro Gly Thr Met Val Thr Val Ser Ser
    130                 135                 140
```

<210> SEQ ID NO 20
<211> LENGTH: 384
<212> TYPE: DNA
<213> ORGANISM: Mus musculus

<400> SEQUENCE: 20

```
atgaacgtgc ccactcaact ccttgggttg ctgcttctct ggcttacagg tggtaaatgt    60
gacatccaga tgacacagtc tcctgcctcc ctgtctgcat ctctggaaga aattgtcacc   120
atcacatgcc aggcaagcca ggacattggt aattacttat catggtatca gcagaaacca   180
gggaaatctc ctcagctcct gatccatagt gcaaccagct ggcagatggg gtcccatca    240
aggttcagcg gcagtagatc tggcacacag tattctctta agatcaacag actacaggtt   300
gaagatactg gaatctatta ctgtctacag cattatagtt ctccgttcac gtttggagct   360
gggaccaagc tggaactgaa acgg                                          384
```

<210> SEQ ID NO 21
<211> LENGTH: 128
<212> TYPE: PRT
<213> ORGANISM: Mus musculus

<400> SEQUENCE: 21

```
Met Asn Val Pro Thr Gln Leu Leu Gly Leu Leu Leu Leu Trp Leu Thr
  1               5                  10                  15

Gly Gly Lys Cys Asp Ile Gln Met Thr Gln Ser Pro Ala Ser Leu Ser
             20                  25                  30

Ala Ser Leu Glu Glu Ile Val Thr Ile Thr Cys Gln Ala Ser Gln Asp
         35                  40                  45

Ile Gly Asn Tyr Leu Ser Trp Tyr Gln Gln Lys Pro Gly Lys Ser Pro
 50                  55                  60

Gln Leu Leu Ile His Ser Ala Thr Ser Leu Ala Asp Gly Val Pro Ser
 65                  70                  75                  80

Arg Phe Ser Gly Ser Arg Ser Gly Thr Gln Tyr Ser Leu Lys Ile Asn
                 85                  90                  95

Arg Leu Gln Val Glu Asp Thr Gly Ile Tyr Tyr Cys Leu Gln His Tyr
            100                 105                 110

Ser Ser Pro Phe Thr Phe Gly Ala Gly Thr Lys Leu Glu Leu Lys Arg
        115                 120                 125
```

<210> SEQ ID NO 22
<211> LENGTH: 432
<212> TYPE: DNA
<213> ORGANISM: Mus musculus

<400> SEQUENCE: 22

```
atggacaggc ttacttcctc attcctactg ctgattgtcc ctgcatatgt cctgtctcag      60
gttactctga aagagtctgg ccctgggata ttgcagccct cccagaccct cagtctgact     120
tgcactttct ctgggttttc actgaacact catggtatgg ctgtgggctg gattcgtcag     180
ccttcaggga agggtctgga gtggctggca aatatttggt gggatgatga taagtactac     240
aatccatctc tgaaaaaccg gctcacaatc tccaaggaca cctccaacaa ccaagcattc     300
ctcaggatca ccaatgtgga cactgcagat actgccacat actactgtac tcggatgaag     360
gaattcgggt cacaggacta ttactatgtt atggatgcct ggggtcaagg agcttcagtc     420
actgtctcct ca                                                         432
```

<210> SEQ ID NO 23
<211> LENGTH: 144
<212> TYPE: PRT
<213> ORGANISM: Mus musculus

<400> SEQUENCE: 23

```
Met Asp Arg Leu Thr Ser Ser Phe Leu Leu Ile Val Pro Ala Tyr
  1               5                  10                  15
Val Leu Ser Gln Val Thr Leu Lys Glu Ser Gly Pro Gly Ile Leu Gln
             20                  25                  30
Pro Ser Gln Thr Leu Ser Leu Thr Cys Thr Phe Ser Gly Phe Ser Leu
         35                  40                  45
Asn Thr His Gly Met Ala Val Gly Trp Ile Arg Gln Pro Ser Gly Lys
     50                  55                  60
Gly Leu Glu Trp Leu Ala Asn Ile Trp Trp Asp Asp Asp Lys Tyr Tyr
 65                  70                  75                  80
Asn Pro Ser Leu Lys Asn Arg Leu Thr Ile Ser Lys Asp Thr Ser Asn
                 85                  90                  95
Asn Gln Ala Phe Leu Arg Ile Thr Asn Val Asp Thr Ala Asp Thr Ala
            100                 105                 110
Thr Tyr Tyr Cys Thr Arg Met Lys Glu Phe Gly Ser Gln Asp Tyr Tyr
        115                 120                 125
Tyr Val Met Asp Ala Trp Gly Gln Gly Ala Ser Val Thr Val Ser Ser
    130                 135                 140
```

<210> SEQ ID NO 24
<211> LENGTH: 393
<212> TYPE: DNA
<213> ORGANISM: Mus musculus

<400> SEQUENCE: 24

```
atgaaagtgc tggtaggct gctggtgctg ttgttttgga ttccagcttc caggactgat      60
attgtgttga cacaaactcc aggttccctg tctgtcacac ttggagatca agcttctata    120
tcttgcaggt ctagtcagag cctggaatat agtgatggat acactttctc tggaatggta    180
ctacagaagc caggccagtc tccacagctc ctcatctatg agtttccaa ccgatttct     240
ggggtcccag acaggttcat tgcagtgggg tcagggacag atttcaccct caagatcagc    300
agagtagagc ctgaggactt gggagtttat tactgcttcc aagctacaca tgagtacacg    360
tttggagctg ggaccaagct ggaactgaaa cgg                                  393
```

<210> SEQ ID NO 25
<211> LENGTH: 131
<212> TYPE: PRT
<213> ORGANISM: Mus musculus

<400> SEQUENCE: 25

Met Lys Val Pro Gly Arg Leu Leu Val Leu Phe Trp Ile Pro Ala
1               5                   10                  15

Ser Arg Thr Asp Ile Val Leu Thr Gln Thr Pro Gly Ser Leu Ser Val
            20                  25                  30

Thr Leu Gly Asp Gln Ala Ser Ile Ser Cys Arg Ser Ser Gln Ser Leu
        35                  40                  45

Glu Tyr Ser Asp Gly Tyr Thr Phe Leu Glu Trp Tyr Leu Gln Lys Pro
    50                  55                  60

Gly Gln Ser Pro Gln Leu Leu Ile Tyr Gly Val Ser Asn Arg Phe Ser
65                  70                  75                  80

Gly Val Pro Asp Arg Phe Ile Gly Ser Gly Ser Gly Thr Asp Phe Thr
                85                  90                  95

Leu Lys Ile Ser Arg Val Glu Pro Glu Asp Leu Gly Val Tyr Tyr Cys
            100                 105                 110

Phe Gln Ala Thr His Glu Tyr Thr Phe Gly Ala Gly Thr Lys Leu Glu
        115                 120                 125

Leu Lys Arg
    130

<210> SEQ ID NO 26
<211> LENGTH: 417
<212> TYPE: DNA
<213> ORGANISM: Mus musculus

<400> SEQUENCE: 26
atgtacttca gcatcagctt ggttttcctt gtgctcattt taaaaagtgt ccagtgtgag      60
gtacagctgg tggagtctgg aggaggctta gtgcagcctg aaagtccct  gaaactctcc    120 tgttcagcct ctggattcac attcagtaac tttggcatgc actggatacg ccaagctcca    180
ggaaaggggc tagattgggt tgcatacatt agtagtaaca acggtacagt ctatgcagac    240
gctgtgaagg gccggttcac catctccaga gacaatgcaa agaacaccct gtacctgcat    300
ctcagcagtc tgaagtctga agacactgcc atctattact gtgcaagaag ttattactat    360
agcagctata tcccttttga ttactggggc caaggagtca tggtcacagt ctcctca      417

<210> SEQ ID NO 27
<211> LENGTH: 139
<212> TYPE: PRT
<213> ORGANISM: Mus musculus

<400> SEQUENCE: 27

Met Tyr Phe Ser Ile Ser Leu Val Phe Leu Val Leu Ile Leu Lys Ser
1               5                   10                  15

Val Gln Cys Glu Val Gln Leu Val Glu Ser Gly Gly Gly Leu Val Gln
            20                  25                  30

Pro Gly Lys Ser Leu Lys Leu Ser Cys Ser Ala Ser Gly Phe Thr Phe
        35                  40                  45

Ser Asn Phe Gly Met His Trp Ile Arg Gln Ala Pro Gly Lys Gly Leu
    50                  55                  60

Asp Trp Val Ala Tyr Ile Ser Ser Asn Asn Gly Thr Val Tyr Ala Asp
65                  70                  75                  80

```
Ala Val Lys Gly Arg Phe Thr Ile Ser Arg Asp Asn Ala Lys Asn Thr
                85                  90                  95

Leu Tyr Leu His Leu Ser Ser Leu Lys Ser Glu Asp Thr Ala Ile Tyr
            100                 105                 110

Tyr Cys Ala Arg Ser Tyr Tyr Ser Ser Tyr Ile Pro Phe Asp Tyr
        115                 120                 125

Trp Gly Gln Gly Val Met Val Thr Val Ser Ser
    130                 135

<210> SEQ ID NO 28
<211> LENGTH: 390
<212> TYPE: DNA
<213> ORGANISM: Mus musculus

<400> SEQUENCE: 28
atggacatga gggcccatac tcagtttctt gggttcttgt ggctcttgtt tgcaggtgcc    60
agatgcgaca tccagatgac ccagtctcca tcctccatgt ctgtatctct gggagacaga   120
gtcactatta cttgtcgggc aagtcaagac attggaaatt atttaaactg gtaccagcag   180
aaaccagaaa aatctcctaa gctcatgatt tatggtgcaa ccaacttgga agatggggtc   240
ccatcaaggc tcagtggcag taggtctggg tcagattatt ctctcaccat caacagcctg   300
gagtctgaag atacaggaat ctatttctgt ctacagcata acagtatcc gttcacgttc    360 ggttctggga ccaagctgga gatcaaacgg                                    390

<210> SEQ ID NO 29
<211> LENGTH: 130
<212> TYPE: PRT
<213> ORGANISM: Mus musculus

<400> SEQUENCE: 29

Met Asp Met Arg Ala His Thr Gln Phe Leu Gly Phe Leu Trp Leu Leu
1               5                   10                  15

Phe Ala Gly Ala Arg Cys Asp Ile Gln Met Thr Gln Ser Pro Ser Ser
            20                  25                  30

Met Ser Val Ser Leu Gly Asp Arg Val Thr Ile Thr Cys Arg Ala Ser
        35                  40                  45

Gln Asp Ile Gly Asn Tyr Leu Asn Trp Tyr Gln Gln Lys Pro Glu Lys
    50                  55                  60

Ser Pro Lys Leu Met Ile Tyr Gly Ala Thr Asn Leu Glu Asp Gly Val
65                  70                  75                  80

Pro Ser Arg Leu Ser Gly Ser Arg Ser Gly Ser Asp Tyr Ser Leu Thr
                85                  90                  95

Ile Asn Ser Leu Glu Ser Glu Asp Thr Gly Ile Tyr Phe Cys Leu Gln
            100                 105                 110

His Lys Gln Tyr Pro Phe Thr Phe Gly Ser Gly Thr Lys Leu Glu Ile
        115                 120                 125

Lys Arg
    130

<210> SEQ ID NO 30
<211> LENGTH: 429
<212> TYPE: DNA
<213> ORGANISM: Mus musculus
```

<400> SEQUENCE: 30

```
atgggttgga gctgtatcat cttctttctg gtagcaacag ctacaggtgt gcactcccag      60
gtccagctgc agcagtctgg gcctgaggtg gtgaggcctg ggtctcagt gaagatttcc     120
tgcaagggtt ccggctacac attcactgat tatgctatgc actgggtgaa gcagagtcat    180
gcaaagagtc cagagtggat tggagttatt agtactaaca gtggtaatgc aatctacaag    240
cagaagttta aggacaaggc cacaatgact gtagacaagt cctccagcac agcctatatg    300
gaacttgcca gattgacatc tgaggattct gccatctatt actgtgccag agggcgtccc    360
gattactacg gtagtagcca ctggtacttc gatgtctggg gcgcagggac cacggtcacc    420
gtctcctca                                                             429
```

<210> SEQ ID NO 31
<211> LENGTH: 143
<212> TYPE: PRT
<213> ORGANISM: Mus musculus

<400> SEQUENCE: 31

```
Met Gly Trp Ser Cys Ile Ile Phe Phe Leu Val Ala Thr Ala Thr Gly
1               5                   10                  15
Val His Ser Gln Val Gln Leu Gln Gln Ser Gly Pro Glu Val Val Arg
            20                  25                  30
Pro Gly Val Ser Val Lys Ile Ser Cys Lys Gly Ser Gly Tyr Thr Phe
        35                  40                  45
Thr Asp Tyr Ala Met His Trp Val Lys Gln Ser His Ala Lys Ser Pro
    50                  55                  60
Glu Trp Ile Gly Val Ile Ser Thr Asn Ser Gly Asn Ala Ile Tyr Lys
65                  70                  75                  80
Gln Lys Phe Lys Asp Lys Ala Thr Met Thr Val Asp Lys Ser Ser Ser
                85                  90                  95
Thr Ala Tyr Met Glu Leu Ala Arg Leu Thr Ser Glu Asp Ser Ala Ile
            100                 105                 110
Tyr Tyr Cys Ala Arg Gly Arg Pro Asp Tyr Tyr Gly Ser Ser His Trp
        115                 120                 125
Tyr Phe Asp Val Trp Gly Ala Gly Thr Thr Val Thr Val Ser Ser
    130                 135                 140
```

<210> SEQ ID NO 32
<211> LENGTH: 384
<212> TYPE: DNA
<213> ORGANISM: Mus musculus

<400> SEQUENCE: 32

```
atggttttca cacctcagat acttggactt atgctttttt ggatttcagc ctccagaggt      60
gatattgtgc taactcagtc tccagccacc ctgtctgtga ctccaggaga tagcgtcagt    120
ctttcctgca gggccagcca agtattagc aacaacctac actggtatca acaaaaatca     180
catgaatctc caagacttct catcaagtat acttcccagt ccatctctgg atccctcc       240
aggttcagtg gcagtggatc aggacagat tcactctca gtatcaacag tgtggagact       300
gaagattttg gaatgtattt ctgtcaacag agtgacagct ggccgctcac gttcggtgct    360
gggaccaagc tggagctgaa acgg                                            384
```

```
<210> SEQ ID NO 33
<211> LENGTH: 128
<212> TYPE: PRT
<213> ORGANISM: Mus musculus

<400> SEQUENCE: 33

Met Val Phe Thr Pro Gln Ile Leu Gly Leu Met Leu Phe Trp Ile Ser
 1               5                  10                  15

Ala Ser Arg Gly Asp Ile Val Leu Thr Gln Ser Pro Ala Thr Leu Ser
             20                  25                  30

Val Thr Pro Gly Asp Ser Val Ser Leu Ser Cys Arg Ala Ser Gln Ser
         35                  40                  45

Ile Ser Asn Asn Leu His Trp Tyr Gln Gln Lys Ser His Glu Ser Pro
     50                  55                  60

Arg Leu Leu Ile Lys Tyr Thr Ser Gln Ser Ile Ser Gly Ile Pro Ser
65                  70                  75                  80

Arg Phe Ser Gly Ser Gly Ser Gly Thr Asp Phe Thr Leu Ser Ile Asn
             85                  90                  95

Ser Val Glu Thr Glu Asp Phe Gly Met Tyr Phe Cys Gln Gln Ser Asp
            100                 105                 110

Ser Trp Pro Leu Thr Phe Gly Ala Gly Thr Lys Leu Glu Leu Lys Arg
            115                 120                 125
```

ANTI-CANINE TARC ANTIBODY USED FOR TREATMENT AND DIAGNOSIS OF CANINE ATOPIC DERMATITIS

TECHNICAL FIELD

The present invention relates to an anti-canine TARC antibody for use in the treatment and diagnosis of canine atopic dermatitis, and a method of using the same.

BACKGROUND ART

Atopic dermatitis is a disease which often has a predisposing factor of atopy and repeats chronic eczematous skin lesions over a long period of time. In addition, with regard to hematological findings, atopic dermatitis has abnormalities such as an increase in the eosinophil count in peripheral blood and the high serum IgE value. Immunological abnormality and non-immunological abnormality have been reported as main factors for atopic dermatitis. In recent years, atopic dermatitis has increased not only in humans, but also in pet animals such as dogs, and thus, it has been desired to establish a method for detecting or treating such atopic dermatitis.

Chemokine is a substance associated with atopic dermatitis. There have been reports regarding macrophage-derived chemokine (see Patent Literature 1 and Patent Literature 2). The term "chemokine" is a general name for cytokines having a molecular weight of approximately 8 to 14 kDa and exhibiting chemotactic activity on leucocytes. As a mediator that is in charge of liaison between inflammatory cells, the chemokine plays a central role for the development and progression of various inflammations. The chemokine is broadly divided into four types of chemokines, namely, C, CC, CXC and CX3C, based on a structural difference in four cysteine sequences. Such chemokines each have receptors, and the receptors are also broadly divided into a C chemokine receptor (XCR) for C chemokine, a CC chemokine receptor (CCR) for CC chemokine, a CXC chemokine receptor (CXCR) for CXC chemokine, and a CX3C chemokine receptor (CX3CR) for CX3C chemokine. It has been considered that, as a result of the interaction of chemokine with its receptor, cells having a receptor corresponding to each chemokine migrate, and play an important role for formation and/or maintenance of a pathologic condition. It has been considered that, among these chemokines, TARC (Thymus Activation-Regulated Chemokine) binding to a CC chemokine receptor 4 (CCR4) that is expressed specifically to the helper T cell Th2 is particularly highly associated with atopic dermatitis. For example, it has been reported that CD4-positive T cells that infiltrate into the affected area of atopic dermatitis patients are positive for CCR4, and also that CCR4-positive memory T cells in peripheral blood are significantly increased in atopic dermatitis patients, in comparison to healthy subjects. Moreover, it has also been reported that the CCR4-positive cell count in peripheral blood is correlated with the eosinophil count, the IgE value, and clinical severity. Furthermore, it has also been reported that the blood TARC value is high and generation of TARC in the affected area is promoted in human atopic dermatitis patients (see Patent Literature 3 and Patent Literature 4).

These reports suggest that TARC would become a disease marker for atopic dermatitis, and that TARC can be a therapeutic target of atopic dermatitis. On the other hand, there are also reports regarding the expression of TARC in a healthy area. Hence, the usefulness of TARC has not yet been sufficiently studied.

Further, the previous reports have been related to studies conducted regarding atopic dermatitis model mice and humans. However, the atopic dermatitis developing mechanism is not always the same among animal species, and thus, it has been desired to establish a diagnostic method and a therapeutic method, which are specific to dogs.

Regarding canine TARC, Maeda et al. (see Non Patent Literature 1) have determined the amino acid sequence and the DNA sequence of mRNA. However, an anti canine TARC antibody suitable for detection of atopic dermatitis has not been obtained. On the other hand, the anti-TARC antibodies of other species such as humans have been commercially available, but these commercially available antibodies have been problematic in that they do not react with canine TARC. In addition, it has been pointed out that such commercially available anti-TARC antibodies are problematic in that the affinity with TARC is insufficient, and that a clear staining image cannot be obtained particularly upon the immunostaining of cellular tissues.

CITATION LIST

Patent Literature

Patent Literature 1: JP Patent Publication (Kohyo) No. 2001-520002 A
Patent Literature 2: JP Patent Publication (Kohyo) No. 10-507646 A (1998)
Patent Literature 3: EP1221618A1
Patent Literature 4: International Publication WO 02/53758

Non Patent Literature

Non Patent Literature 1: J. Vet. Med. Sci. 63(9): 1035-1038, 2001
Non Patent Literature 2: J. Invest. Dermatol. 115(4): 640-646, 2000
Non Patent Literature 3: Uchida et al.; International Immunology. 14(12): 1431-1438, 2002

SUMMARY OF INVENTION

Technical Problem

It is an object of the present invention to provide an anti-canine TARC antibody for use in the treatment and diagnosis of canine atopic dermatitis, and a method for treating or diagnosing canine atopic dermatitis using the same.

Solution to Problem

The present inventors have considered that TARC would also be associated with canine atopic dermatitis. Thus, the inventors have produced an anti-canine TARC monoclonal antibody, using recombinant canine TARC that had been produced based on the previously known canine TARC gene sequence. Thereafter, the inventors have selected an anti-canine TARC monoclonal antibody capable of detecting canine TARC with high sensitivity and high specificity from a plurality of clones, and have then determined the sequence of the variable region of the monoclonal antibody, thereby completing the present invention.

Specifically, the present invention is as follows.
[1] An anti-canine TARC monoclonal antibody binding to canine TARC, comprising a heavy chain variable region consisting of the amino acid sequence shown in SEQ ID NO:

2 and a light chain variable region consisting of the amino acid sequence shown in SEQ ID NO: 4, or a functional fragment thereof binding to canine TARC.

[2] An anti-canine TARC monoclonal antibody binding to canine TARC, comprising a heavy chain variable region consisting of an amino acid sequence having a sequence identity of 90% or more with the amino acid sequence shown in SEQ ID NO: 2 and having a binding activity to canine TARC, and a light chain variable region consisting of an amino acid sequence having a sequence identity of 90% or more with the amino acid sequence shown in SEQ ID NO: 4 and having a binding activity to canine TARC, or a functional fragment thereof binding to canine TARC.

[3] An anti-canine TARC monoclonal antibody binding to canine TARC, comprising a heavy chain variable region encoded by DNA consisting of the nucleotide sequence shown in SEQ ID NO: 1 and a light chain variable region encoded by DNA consisting of the nucleotide sequence shown in SEQ ID NO: 3, or a functional fragment thereof binding to canine TARC.

[4] An anti-canine TARC monoclonal antibody binding to canine TARC, comprising a heavy chain variable region having a binding activity to canine TARC, which is encoded by a nucleotide sequence having a sequence identity of 90% or more with the nucleotide sequence shown in SEQ ID NO: 1, and a light chain variable region having a binding activity to canine TARC, which is encoded by a nucleotide sequence having a sequence identity of 90% or more with the nucleotide sequence shown in SEQ ID NO: 3, or a functional fragment thereof binding to canine TARC.

[5] The anti-canine TARC monoclonal antibody according to any one of the above [1] to [4], or a functional fragment thereof binding to canine TARC, wherein the heavy chain constant region and the light chain constant region are the constant regions of a canine IgG antibody.

[6] The anti-canine TARC monoclonal antibody binding to canine TARC according to any one of the above [1] to [5], or a functional fragment thereof binding to canine TARC, wherein the functional fragment is a peptide fragment selected from the group consisting of Fab, Fab', F(ab')$_2$, a disulfide bond Fv (dsFv), a dimerized V region (diabody), a single chain Fv (scFv), and CDR.

[7] A polypeptide that is the heavy chain variable region of an anti-canine TARC monoclonal antibody, the polypeptide consisting of the amino acid sequence shown in SEQ ID NO: 2.

[8] A polypeptide that is the light chain variable region of an anti-canine TARC monoclonal antibody, the polypeptide consisting of the amino acid sequence shown in SEQ ID NO: 4.

[9] A polynucleotide encoding the heavy chain variable region of an anti-canine TARC monoclonal antibody, the polynucleotide consisting of the DNA sequence shown in SEQ ID NO: 1.

[10] A polynucleotide encoding the light chain variable region of an anti-canine TARC monoclonal antibody, the polynucleotide consisting of the DNA sequence shown in SEQ ID NO: 3.

[11] A vector comprising the polynucleotide according to the above [9], or the polynucleotide according to the above [10], or the polynucleotide according to the above [9] and the polynucleotide according to the above [10].

[12] A cell comprising the vector according to the above [11].

[13] A method for producing an anti-canine TARC monoclonal antibody, which comprises: linking DNA encoding the heavy chain variable region of an anti-canine TARC monoclonal antibody, consisting of the DNA sequence shown in SEQ ID NO: 1, with DNA encoding the heavy chain constant region of the antibody; linking DNA encoding the light chain variable region of an anti-canine TARC monoclonal antibody, consisting of the DNA sequence shown in SEQ ID NO: 3, with DNA encoding the light chain constant region of the antibody; inserting the obtained DNA construct into an expression vector; and transforming a host cell or a host animal with the vector, to produce the antibody from the host cell or the host animal.

[14] An immunoassay for measuring canine TARC by using the anti-canine TARC monoclonal antibody binding to canine TARC according to any one of the above [1] to [6], or a functional fragment thereof binding to canine TARC.

[15] The immunoassay according to the above [14], which is ELISA.

[16] A detection reagent for canine atopic dermatitis, comprising the anti-canine TARC monoclonal antibody binding to canine TARC according to any one of the above [1] to [6], or a functional fragment thereof binding to canine TARC.

[17] A method for detecting canine atopic dermatitis, which comprises measuring TARC in blood, serum or plasma collected from a canine, by using the anti-canine TARC monoclonal antibody binding to canine TARC according to any one of the above [1] to [6], or a functional fragment thereof binding to canine TARC.

[18] An anti-canine TARC monoclonal antibody binding to canine TARC, comprising a heavy chain variable region and a light chain variable region described in any one of the following (i) to (iv), or a functional fragment thereof binding to canine TARC:

(i) a heavy chain variable region consisting of the amino acid sequence shown in SEQ ID NO: 19, and a light chain variable region consisting of the amino acid sequence shown in SEQ ID NO: 21;

(ii) a heavy chain variable region consisting of the amino acid sequence shown in SEQ ID NO: 23, and a light chain variable region consisting of the amino acid sequence shown in SEQ ID NO: 25;

(iii) a heavy chain variable region consisting of the amino acid sequence shown in SEQ ID NO: 27, and a light chain variable region consisting of the amino acid sequence shown in SEQ ID NO: 29; and (iv) a heavy chain variable region consisting of the amino acid sequence shown in SEQ ID NO: 31, and a light chain variable region consisting of the amino acid sequence shown in SEQ ID NO: 33.

[19] An anti-canine TARC monoclonal antibody binding to canine TARC, comprising a heavy chain variable region and a light chain variable region described in any one of the following (i) to (iv), or a functional fragment thereof binding to canine TARC:

(i) a heavy chain variable region consisting of an amino acid sequence having a sequence identity of 90% or more with the amino acid sequence shown in SEQ ID NO: 19 and having a binding activity to canine TARC, and a light chain variable region consisting of an amino acid sequence having a sequence identity of 90% or more with the amino acid sequence shown in SEQ ID NO: 21 and having a binding activity to canine TARC;

(ii) a heavy chain variable region consisting of an amino acid sequence having a sequence identity of 90% or more with the amino acid sequence shown in SEQ ID NO: 23 and having a binding activity to canine TARC, and a light chain variable region consisting of an amino acid sequence having a sequence identity of 90% or more with the amino acid sequence shown in SEQ ID NO: 25 and having a binding activity to canine TARC;
(iii) a heavy chain variable region consisting of an amino acid sequence having a sequence identity of 90% or more with the amino acid sequence shown in SEQ ID NO: 27 and having a binding activity to canine TARC, and a light chain variable region consisting of an amino acid sequence having a sequence identity of 90% or more with the amino acid sequence shown in SEQ ID NO: 29 and having a binding activity to canine TARC; and
(iv) a heavy chain variable region consisting of an amino acid sequence having a sequence identity of 90% or more with the amino acid sequence shown in SEQ ID NO: 31 and having a binding activity to canine TARC, and a light chain variable region consisting of an amino acid sequence having a sequence identity of 90% or more with the amino acid sequence shown in SEQ ID NO: 33 and having a binding activity to canine TARC.

[20] An anti-canine TARC monoclonal antibody binding to canine TARC, comprising a heavy chain variable region and a light chain variable region described in any one of the following (i) to (iv), or a functional fragment thereof binding to canine TARC:
(i) a heavy chain variable region encoded by DNA consisting of the nucleotide sequence shown in SEQ ID NO: 18, and a light chain variable region encoded by DNA consisting of the nucleotide sequence shown in SEQ ID NO: 20;
(ii) a heavy chain variable region encoded by DNA consisting of the nucleotide sequence shown in SEQ ID NO: 22, and a light chain variable region encoded by DNA consisting of the nucleotide sequence shown in SEQ ID NO: 24;
(iii) a heavy chain variable region encoded by DNA consisting of the nucleotide sequence shown in SEQ ID NO: 26, and a light chain variable region encoded by DNA consisting of the nucleotide sequence shown in SEQ ID NO: 28; and
(iv) a heavy chain variable region encoded by DNA consisting of the nucleotide sequence shown in SEQ ID NO: 30, and a light chain variable region encoded by DNA consisting of the nucleotide sequence shown in SEQ ID NO: 32.

[21] An anti-canine TARC monoclonal antibody binding to canine TARC, comprising a heavy chain variable region and a light chain variable region described in any one of the following (i) to (iv), or a functional fragment thereof binding to canine TARC:
(i) a heavy chain variable region having a binding activity to canine TARC, which is encoded by a nucleotide sequence having a sequence identity of 90% or more with the nucleotide sequence shown in SEQ ID NO: 18, and a light chain variable region having a binding activity to canine TARC, which is encoded by a nucleotide sequence having a sequence identity of 90% or more with the nucleotide sequence shown in SEQ ID NO: 20;
(ii) a heavy chain variable region having a binding activity to canine TARC, which is encoded by a nucleotide sequence having a sequence identity of 90% or more with the nucleotide sequence shown in SEQ ID NO: 22, and a light chain variable region having a binding activity to canine TARC, which is encoded by a nucleotide sequence having a sequence identity of 90% or more with the nucleotide sequence shown in SEQ ID NO: 24;
(iii) a heavy chain variable region having a binding activity to canine TARC, which is encoded by a nucleotide sequence having a sequence identity of 90% or more with the nucleotide sequence shown in SEQ ID NO: 26, and a light chain variable region having a binding activity to canine TARC, which is encoded by a nucleotide sequence having a sequence identity of 90% or more with the nucleotide sequence shown in SEQ ID NO: 28; and
(iv) a heavy chain variable region having a binding activity to canine TARC, which is encoded by a nucleotide sequence having a sequence identity of 90% or more with the nucleotide sequence shown in SEQ ID NO: 30, and a light chain variable region having a binding activity to canine TARC, which is encoded by a nucleotide sequence having a sequence identity of 90% or more with the nucleotide sequence shown in SEQ ID NO: 32.

[22] The anti-canine TARC monoclonal antibody according to any one of the above [18] to [21], or a functional fragment thereof binding to canine TARC, wherein the heavy chain constant region and the light chain constant region are the constant regions of a canine IgG antibody.

[23] The anti-canine TARC monoclonal antibody binding to canine TARC according to any one of the above [18] to [22], or a functional fragment thereof binding to canine TARC, wherein the functional fragment is a peptide fragment selected from the group consisting of Fab, Fab', F(ab')$_2$, a disulfide bond Fv (dsFv), a dimerized V region (diabody), a single chain Fv (scFv), and CDR.

[24] A polypeptide that is the heavy chain variable region of an anti-canine TARC monoclonal antibody, the polypeptide consisting of the amino acid sequence shown in SEQ ID NO: 19, 23, 27 or 31.

[25] A polypeptide that is the light chain variable region of an anti-canine TARC monoclonal antibody, the polypeptide consisting of the amino acid sequence shown in SEQ ID NO: 21, 25, 29 or 33.

[26] A polynucleotide encoding the heavy chain variable region of an anti-canine TARC monoclonal antibody, the polynucleotide consisting of the DNA sequence shown in SEQ ID NO: 18, 22, 26 or 30.

[27] A polynucleotide encoding the light chain variable region of an anti-canine TARC monoclonal antibody, the polynucleotide consisting of the DNA sequence shown in SEQ ID NO: 20, 24, 28 or 32.

[28] A vector comprising the polynucleotide according to the above [24], or the polynucleotide according to the above [25], or the polynucleotide according to the above [26] and the polynucleotide according to the above [27].

[29] A cell comprising the vector according to the above [28].

[30] A method for producing an anti-canine TARC monoclonal antibody, which comprises: performing the linking of any one of the following (i) to (iv):
(i) linking DNA encoding the heavy chain variable region of an anti-canine TARC monoclonal antibody, consisting of the DNA sequence shown in SEQ ID NO: 18, with DNA encoding the heavy chain constant region of the antibody, and linking DNA encoding the light chain variable region of an anti-canine TARC monoclonal antibody, consisting of the DNA sequence shown in SEQ ID NO: 20, with DNA encoding the light chain constant region of the antibody,
(ii) linking DNA encoding the heavy chain variable region of an anti-canine TARC monoclonal antibody, consisting of the DNA sequence shown in SEQ ID NO: 22, with DNA encoding the heavy chain constant region of the antibody, and linking DNA encoding the light chain variable region of an anti-canine TARC monoclonal antibody, consisting of the DNA sequence shown in SEQ ID NO: 24, with DNA encoding the light chain constant region of the antibody,
(iii) linking DNA encoding the heavy chain variable region of an anti-canine TARC monoclonal antibody, consisting of the DNA sequence shown in SEQ ID NO: 26, with DNA encoding the heavy chain constant region of the antibody, and linking DNA encoding the light chain variable region of an anti-canine TARC monoclonal antibody, consisting of the DNA sequence shown in SEQ ID NO: 28, with DNA encoding the light chain constant region of the antibody, or (iv) linking DNA encoding the heavy chain variable region of an anti-canine TARC monoclonal antibody, consisting of the DNA sequence shown in SEQ ID NO: 30, with DNA encoding the heavy chain constant region of the antibody, and linking DNA encoding the light chain variable region of an anti-canine TARC monoclonal antibody, consisting of the DNA sequence shown in SEQ ID NO: 32, with DNA encoding the light chain constant region of the antibody; and inserting the obtained DNA construct into an expression vector; and transforming a host cell or a host animal with the vector, to produce the antibody from the host cell or the host animal.

[31] An immunoassay for measuring canine TARC by using the anti-canine TARC monoclonal antibody binding to canine TARC according to any one of the above [18] to [23], or a functional fragment thereof binding to canine TARC.

[32] The immunoassay according to the above [31], which is ELISA.

[33] A detection reagent for canine atopic dermatitis, comprising the anti-canine TARC monoclonal antibody binding to canine TARC according to any one of the above [18] to [23], or a functional fragment thereof binding to canine TARC.

[34] A method for detecting canine atopic dermatitis, which comprises measuring TARC in blood, serum or plasma collected from a canine, by using the anti-canine TARC monoclonal antibody binding to canine TARC according to any one of the above [18] to [23], or a functional fragment thereof binding to canine TARC.

The present description includes part or all of the contents as disclosed in Japanese Patent Application No. 2015-203123, which is a priority document of the present application.

Advantageous Effects of Invention

The canine TARC monoclonal antibody of the present invention solves the problem that a commercially available TARC monoclonal antibody does not react with canine TARC. Moreover, since the reactivity obtained when the concentration of canine TARC is changed linearly relates to the concentration, canine TARC can be measured using the present canine TARC monoclonal antibody with higher sensitivity and higher specificity than in the case of using the conventionally known TARC antibody. Accordingly, by using the antibody of the present invention, highly sensitive ELISA can be constructed, and a means that is effective for the diagnosis of canine atopic dermatitis can be provided. Furthermore, the anti-canine TARC monoclonal antibody of the present invention is also effective for the treatment of canine atopic dermatitis.

BRIEF DESCRIPTION OF DRAWINGS

FIG. 4 is a view showing the sequences of primers used in the production of recombinant anti-canine TARC monoclonal antibodies.

DESCRIPTION OF EMBODIMENTS

Figure 1:
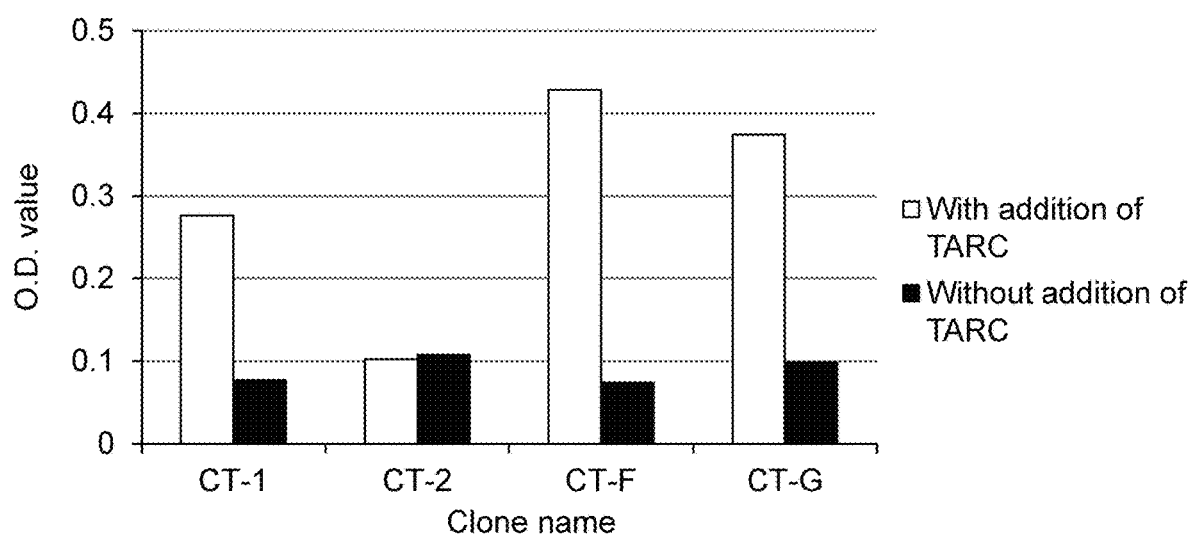
FIG. 1 is a view showing the reactivity of an anti-canine TARC monoclonal antibody with canine TARC.

Hereinafter, the present invention will be described in detail.

The present invention relates to an anti-canine TARC monoclonal antibody specifically binding to canine TARC, wherein the anti-canine TARC monoclonal antibody comprises the heavy chain variable region and the light chain (κ chain) variable region of a monoclonal antibody CT-1 specifically binding to canine TARC.

In addition, the present invention includes a polypeptide that is the heavy chain variable region or the light chain (κ chain) variable region of the above-described CT-1 antibody, and a polynucleotide encoding those variable regions.

Moreover, the present invention relates to an anti-canine TARC monoclonal antibody specifically binding to canine TARC, wherein the anti-canine TARC monoclonal antibody comprises the heavy chain variable region and the light chain (κ chain) variable region of a monoclonal antibody R1, R5, R7 or CT-3 specifically binding to canine TARC.

Furthermore, the present invention includes a polypeptide that is the heavy chain variable region or the light chain (κ chain) variable region of the above-described antibody R1, R5, R7 or CT-3, and a polynucleotide encoding those variable regions.

The antibody of the present invention includes a functional fragment of the antibody, or a modified product thereof. For example, the functional fragment of the antibody is a fragment of the antibody, which is capable of specifically binding to an antigen. Examples of the functional fragment include Fab, F(ab')2, Fv, Fab/c having one Fab and complete Fc, a single chain Fv (scFv) in which the Fv of an H chain is ligated with that of an L chain with a suitable linker, and CDR. The polynucleotide includes both DNA and RNA.

The nucleotide sequence of DNA encoding the heavy chain variable region of a CT-1 antibody consists of the nucleotide sequence shown in SEQ ID NO: 1, and the amino acid sequence of the heavy chain variable region consists of the amino acid sequence shown in SEQ ID NO: 2. In addition, the nucleotide sequence of DNA encoding the light chain variable region of a CT-1 antibody consists of the nucleotide sequence shown in SEQ ID NO: 3, and the amino acid sequence of the light chain variable region consists of the amino acid sequence shown in SEQ ID NO: 4.

The nucleotide sequence of DNA encoding the heavy chain variable region of an R1 antibody consists of the nucleotide sequence shown in SEQ ID NO: 18, and the amino acid sequence of the heavy chain variable region consists of the amino acid sequence shown in SEQ ID NO: 19. In addition, the nucleotide sequence of DNA encoding the light chain variable region of an R1 antibody consists of the nucleotide sequence shown in SEQ ID NO: 20, and the amino acid sequence of the light chain variable region consists of the amino acid sequence shown in SEQ ID NO: 21.

The nucleotide sequence of DNA encoding the heavy chain variable region of an R5 antibody consists of the nucleotide sequence shown in SEQ ID NO: 22, and the amino acid sequence of the heavy chain variable region consists of the amino acid sequence shown in SEQ ID NO: 23. In addition, the nucleotide sequence of DNA encoding the light chain variable region of an R5 antibody consists of the nucleotide sequence shown in SEQ ID NO: 24, and the amino acid sequence of the light chain variable region consists of the amino acid sequence shown in SEQ ID NO: 25.

The nucleotide sequence of DNA encoding the heavy chain variable region of an R7 antibody consists of the nucleotide sequence shown in SEQ ID NO: 26, and the amino acid sequence of the heavy chain variable region consists of the amino acid sequence shown in SEQ ID NO: 27. In addition, the nucleotide sequence of DNA encoding the light chain variable region of an R7 antibody consists of the nucleotide sequence shown in SEQ ID NO: 28, and the amino acid sequence of the light chain variable region consists of the amino acid sequence shown in SEQ ID NO: 29.

The nucleotide sequence of DNA encoding the heavy chain variable region of a CT-3 antibody consists of the nucleotide sequence shown in SEQ ID NO: 30, and the amino acid sequence of the heavy chain variable region consists of the amino acid sequence shown in SEQ ID NO: 31. In addition, the nucleotide sequence of DNA encoding the light chain variable region of a CT-3 antibody consists of the nucleotide sequence shown in SEQ ID NO: 32, and the amino acid sequence of the light chain variable region consists of the amino acid sequence shown in SEQ ID NO: 33.

The heavy chain variable region does not only include a heavy chain variable region consisting of the amino acid sequence shown in SEQ ID NO: 2, 19, 23, 27 or 31, but it also includes a heavy chain variable region, which consists of an amino acid sequence comprising a deletion, substitution or addition of one or several, for example, 1 to 10, preferably 1 to 5, more preferably 1 or 2, and further preferably one amino acid, with respect to the aforementioned amino acid sequence, and which consists of a protein having the activity of the heavy chain variable region of the antibody, namely, a binding activity to canine TARC. The light chain variable region does not only include a light chain variable region consisting of the amino acid sequence shown in SEQ ID NO: 4, 21, 25, 29 or 33, but it also includes a light chain variable region, which consists of an amino acid sequence comprising a deletion, substitution or addition of one or several, for example, 1 to 10, preferably 1 to 5, more preferably 1 or 2, and further preferably one amino acid, with respect to the aforementioned amino acid sequence, and which consists of a protein having the activity of the light chain variable region of the antibody, namely, a binding activity to canine TARC.

The amino acid sequence comprising a deletion, substitution or addition of one or several amino acids, with respect to the amino acid sequence shown in SEQ ID NO: 2, 19, 23, 27 or 31, or 4, 21, 25, 29 or 33, can be an amino acid sequence having a sequence identity of at least 85% or more, preferably 90% or more, more preferably 95% or more, and particularly preferably 97% or more, with the amino acid sequence shown in SEQ ID NO: 2, 19, 23, 27 or 31, or 4, 21, 25, 29 or 33, when the sequence identity is calculated using BLAST (Basic Local Alignment Search Tool at the National Center for Biological Information), etc. (for example, default parameters, namely, initial parameters).

The protein having an amino acid sequence comprising a deletion, substitution or addition of one or several amino acids with respect to the amino acid sequence shown in SEQ ID NO: 2, 19, 23, 27 or 31, or 4, 21, 25, 29 or 33, is substantially identical to a protein having the amino acid sequence shown in SEQ ID NO: 2 or 4.

Moreover, DNA consisting of a nucleotide sequence having a sequence identity of at least 85% or more, preferably 90% or more, more preferably 95% or more, and particularly preferably 97% or more, with the aforementioned nucleotide sequence shown in SEQ ID NO: 1, 18, 22, 26 or 30, or 3, 20, 24, 28 or 32, when the sequence identity is calculated using BLAST (Basic Local Alignment Search Tool at the National Center for Biological Information), etc. (for example, default parameters, namely, initial parameters), and encoding a protein having the activity of the heavy chain variable region or light chain variable region of the antibody, namely, a binding activity to canine TARC, is also included in the DNA encoding the heavy chain variable region or light chain variable region of the antibody of the present invention.

Furthermore, DNA being capable of hybridizing under stringent conditions with DNA consisting of a sequence complementary to the aforementioned DNA consisting of the nucleotide sequence shown in SEQ ID NO: 1, 18, 22, 26 or 30, or 3, 20, 24, 28 or 32, and encoding a protein having the activity of the heavy chain variable region or light chain variable region of the antibody, namely, a binding activity to canine TARC, is also included in the DNA encoding the heavy chain variable region or light chain variable region of the antibody of the present invention. That is to say, the conditions used herein mean conditions under which hybridization is carried out using a DNA-immobilized filter at 68° C. in the presence of 0.7 to 1.0 M NaCl, and washing is then carried out using 0.1 to 2×SSC solution (wherein 1×SSC solution consists of 150 mM NaCl and 15 mM sodium citrate) at 68° C. for identification. Otherwise, this is DNA capable of forming a hybrid by transcribing the DNA on a nitrocellulose membrane according to a Southern blotting method, fixing it thereon, and then reacting it in a hybridization solution [50% formamide, 4×SSC, 50 mM HEPES (pH7.0), 10×Denhardt's solution, and 100 μg/ml salmon sperm DNA] at 42° C. overnight.

The heavy chain variable region or light chain variable region of the anti-canine TARC monoclonal antibody specifically binding to canine TARC of the present invention can be obtained by obtaining anti-canine TARC antibody-producing hybridomas according to a known method using canine TARC as an immunogen and also using mouse or rat cells, then isolating DNA encoding the heavy chain variable region or DNA encoding the light chain variable region from the hybridomas, and then allowing the DNA to express.

The canine TARC used as an immunogen can be produced, for example, by preparing a recombinant vector based on the nucleotide sequence determined by Maeda et al. (J. Vet. Med. Sci. 63(9): 1035-1038, 2001), and then allowing recombinant canine TARC to express using the recombinant vector.

Moreover, the anti-canine TARC monoclonal antibody comprising the above-described heavy chain variable region and light chain variable region, which specifically binds to canine TARC, is constituted with the aforementioned heavy chain variable region and heavy chain constant region and the aforementioned light chain variable region and light chain constant region. The heavy chain constant region is constituted with three domains, $C_H1$, $C_H2$ and $C_H3$. The heavy chain constant region may be an IgG1, IgG2, IgG3, IgG4, IgA, IgE, IgM or IgD constant region, and it is most preferably an IgG1 or IgG4 constant region. The light chain constant region is constituted with a single domain $C_L$. The light chain constant region is a κ or λ constant region.

DNA encoding the antibody is obtained by linking DNA encoding the heavy chain variable region with DNA encoding the heavy chain constant region, and further linking DNA encoding the light chain variable region with DNA encoding the light chain constant region, so that the DNA encoding the antibody can be obtained as DNA encoding a heavy chain and DNA encoding a light chain. The organism species from which the variable region is derived may be different from the organism species from which the constant region is derived. The anti-canine TARC antibody of the present invention includes a chimeric antibody, in which the organism species from which the variable region is derived is different from the organism species from which the constant region is derived. For example, the heavy chain variable region encoded by DNA shown in SEQ ID NO: 1, 18, 22, 26 or 30 and the light chain variable region encoded by DNA shown in SEQ ID NO: 3, 20, 24, 28 or 32 are derived from a mouse. This variable region is linked with DNA encoding the constant region of an antibody derived from a dog, so as to produce a chimeric antibody comprising a mouse-derived variable region and a dog-derived constant region.

The heavy chain variable region or light chain variable region of the present invention can be produced by inserting DNA encoding a heavy chain variable region or DNA encoding a light chain variable region into an expression vector, transforming host cells for expression with the vector, and then culturing the host cells to allow the cells to generate the heavy chain variable region or the light chain variable region.

The anti-canine TARC monoclonal antibody of the present invention can be produced by inserting the aforementioned DNA encoding a heavy chain and DNA encoding a light chain into an expression vector, transforming host cells with the vector, and then culturing the host cells, so as to allow the cells to generate the present anti-canine TARC monoclonal antibody. At this time, the aforementioned DNA encoding a heavy chain and DNA encoding a light chain may be inserted into the same expression vector, and the host cells may be then transformed with the vector. Otherwise, the DNA encoding a heavy chain and DNA encoding a light chain may be inserted into different expression vectors, and the host cells may be then transformed with the two vectors. At this time, DNAs encoding the heavy chain variable region and the light chain variable region may be inserted into a vector, into which DNAs encoding a heavy chain constant region and a light chain constant region bearing a specific isotype have previously been inserted. Moreover, the vector may comprise DNA encoding a signal peptide that promotes the secretion of an antibody from the host cells. In this case, the DNA encoding a signal peptide is linked in-flame with the DNA encoding the antibody. After generation of the antibody, the signal peptide is removed, so that the antibody can be obtained as a mature protein.

At this time, the DNA encoding the heavy chain variable region, the DNA encoding the light chain variable region, DNA obtained by linking the DNA encoding the heavy chain variable region with the DNA encoding the heavy chain constant region, and DNA obtained by linking the DNA encoding the light chain variable region with the DNA encoding the light chain constant region may be operably linked to elements such as a promoter, an enhancer, and a polyadenylation signal. The phrase "operably linked" is used herein to mean that the DNA is linked to elements, so that the elements can play their own functions.

As such promoters and an enhancers, promoters and enhancers derived from Cytomegalovirus (CMV), simian virus 40(SV40), and adenovirus can be used.

The vector used for insertion of the gene of the present invention is not particularly limited, as long as it can replicate in a host such as animal cells, bacteria or yeast. Examples of the vector include a plasmid and a phage. As a vector used for the construction of an expression vector, a known vector can be used. Examples of such a vector include Flexi (registered trademark) vector (Promega), pUC19, pTV118 N (manufactured by Takara Shuzo Co., Ltd.), pUEX2 (manufactured by Amersham), pGEX-4T, pKK233-2 (manufactured by Pharmacia), and pMAM-neo (manufactured by Clontech).

The expression vector can be introduced into host cells according to a known method, so that the host cells can be transformed. Examples of the gene transfer method include an electroporation method, a calcium phosphate precipitation method, and a DEAE-dextran transfection method.

As host cells, both prokaryotic cells such as *Escherichia coli* or *Bacillus subtilis*, and eukaryotic cells such as yeast or animal cells can be used. Among these, eukaryotic cells are preferably used. Examples of the animal cells include HEK293 cells as a human embryonic kidney cell line, Chinese hamster ovary (CHO) cells, Sf 21 cells, Sf 9 cells or TN5 cells, which are lepidopterous insect cells such as silk worm, monkey COS cells, and mouse fibroblasts. An example of the yeast is *Saccharomyces cerevisiae*. Moreover, the variable region or antibody of the present invention can also be produced using animal bodies such as silk worm bodies. Production of the present variable region or antibody using silk worm bodies can be carried out according to a known method.

The expressed and produced antibody may be purified by separation and purification methods used for ordinary proteins. For example, the antibody can be separated and purified by appropriately selecting and combining affinity chromatography, other chromatography, filter, ultrafiltration, salting out, dialysis, and the like (Antibodies A Laboratory Manual. Ed Harlow, David Lane, Cold Spring Harbor Laboratory, 1988). Moreover, an anti-canine TARC antibody is produced in a state in which an affinity tag is attached to the antibody, and the produced antibody is then subjected to affinity chromatography utilizing the affinity tag, so that the antibody can be purified. An example of such an affinity tag sequence is a polyhistidine sequence consisting of, for example, 2 to 12, preferably 4 or more, more preferably 4 to 7, and further preferably 5 or 6 histidines. In this case, by utilizing nickel chelate column chromatography in which nickel is used as a ligand, a synthetic protein can be purified. Furthermore, such an antibody can also be purified by affinity chromatography using a column on which an antibody against polyhistidine is immobilized as a ligand. What is more, an HAT tag, a HN tag or the like, consisting of a sequence containing histidine, can also be used. Further, other affinity tags include a V5 tag, an Xpress tag, an AU1 tag, a T7 tag, a VSV-G tag, a DDDDK tag, an S tag, Cruz Tag 09, Cruz Tag 22, Cruz Tag 41, a Glu-Glu tag, an Ha.11 tag, and a KT3 tag. The present invention also includes an anti-canine TARC antibody, to which these tags bind.

The canine TARC monoclonal antibody of the present invention can be used for both the detection of canine atopic dermatitis and the treatment of canine atopic dermatitis. When the present canine TARC monoclonal antibody is used as a therapeutic agent, it is desired to use the canine TARC monoclonal antibody, which does not provoke an immune response when it is administered into the body of a dog.

Examples of such an antibody include a chimeric antibody comprising the constant region of a dog as a constant region of the antibody, and a caninized antibody in which all variable regions other than constant regions and hypervariable regions are replaced with canine sequences.

The anti-canine TARC monoclonal antibody of the present invention can be used for the diagnosis of canine atopic dermatitis. Specifically, the anti-canine TARC monoclonal antibody of the present invention is used to immunologically detect TARC in a canine biological sample, so as to detect atopic dermatitis. Canine TARC can be detected according to immunoassays known to a person skilled in the art, such as an immunoblotting method, enzyme immunoassays (EIA and ELISA), a radioimmunoassay (RIA), a fluorescent antibody technique, a method of utilizing an agglutination reaction, or an immunochromatography. The term "canine biological sample" is used herein to mean body fluids or tissues, such as serum, plasma, urine, spinal fluid, or lesional tissues.

For example, in the enzyme immunoassay (EIA), an anti-canine TARC monoclonal antibody is immobilized on a carrier such as a microplate, resin beads or magnetic beads by physical adsorption or a chemical bond. The amount of the anti-canine TARC monoclonal antibody immobilized is not particularly limited. When the carrier is a microplate, the immobilized amount of the antibody is desirably several ng to several tens of mg per well. Immobilization can be carried out by dissolving an antibody to be immobilized in a suitable buffer and then allowing the buffer to come into contact with a carrier. For example, when microtiter wells are used, an antibody solution that has been adjusted to a suitable concentration is dispensed into wells of a microtiter plate and then leaving the wells for a certain period of time, so that the antibody can be immobilized on each well. After immobilization of the antibody, in order to prevent non-specific binding during the assay, blocking is preferably carried out using a blocking solution comprising bovine serum albumin, human serum albumin, rabbit serum albumin, or ovalbumin. Subsequently, the immobilized carrier is allowed to react with a sample, the obtained mixture is then washed, and the reaction mixture is then allowed to react with a labeled anti-canine TARC antibody. Labeling can be carried out using an enzyme such as β-D-galactosidase, peroxidase, alkaline phosphatase or glucose oxidase. For example, in the ELISA (Enzyme-Linked ImmunoSorbent Assay), the antibody is immobilized on a microtiter plate having a large number of wells (e.g., 96 wells), and an antigen-antibody reaction is then carried out in each well, so that a large amount of antibody can be measured in a single operation. Moreover, it is also possible to significantly reduce the amounts of an antibody and a sample used. Furthermore, it becomes also possible to use an automatic measuring device such as a full automatic EIA measuring device.

In canine subjects which are affected with atopic dermatitis, the blood TARC level increases. Canine TARC in a biological sample collected from such a canine subject is measured in vitro, and if the TARC level in the biological sample significantly increases, in comparison to the TARC level in a healthy dog, it can be diagnosed that the canine subject is affected with atopic dermatitis. Further, by measuring TARC in a biological sample collected from a canine subject, the risk of being affected with atopic dermatitis can be evaluated. When TARC in a biological sample collected from a canine subject is measured in vitro and the TARC level significantly increases in comparison to a healthy dog, it can be evaluated that the canine subject has a high risk of being affected with atopic dermatitis. That is to say, by measuring TARC in biological samples from canine subjects, it becomes possible to screen for canine subjects having a high risk of being affected with atopic dermatitis and to perform appropriate procedures on the subjects.

At this time, the TARC level in blood collected from a healthy dog has previously been measured, and a cutoff value is determined from the measured value, so that a canine subject can be diagnosed by comparing the TARC level in the biological sample of the canine subject with the cutoff value.

It is also an object of the present invention to provide a kit capable of detecting canine TARC in a canine biological sample, and this kit comprises at least an anti-canine TARC monoclonal antibody. When this kit is based on an enzyme immunoassay, it may comprise an antibody-immobilized carrier, or an antibody may have previously bound to a carrier. In addition, the kit may comprise, as appropriate, a blocking solution, a reaction solution, a reaction termination solution, a reagent for treating a sample, and the like.

The anti-TARC monoclonal antibody of the present invention can also be used to treat canine atopic dermatitis.

The administration form of a preparation comprising the antibody of the present invention is not particularly limited, and the preparation can be administered by oral, parenteral, transmucosal (e.g., sublingual or intraoral administration), local, transdermal, rectal, or inhalation (e.g., nasal or pulmonary inhalation) administration, etc. Examples of the parenteral administration include intravenous, subcutaneous, and intramuscular injections. The local or transdermal preparation is used in the form of powders, an emulsion, a suspension, spray, cream ointment, lotion, paste, etc., or is also used in the form of a medicinal ointment, patch or film. Furthermore, it may also be possible to allow a shampoo or a conditioner to comprise the antibody of the present invention. The amount of the antibody of the present invention necessary for the treatment is different depending on the properties of a pathologic condition to be treated, and the age and condition of a subject. The amount of the present antibody can be finally determined by a veterinarian in charge. For instance, in the case of a local application form such as ointment, the preparation comprises the present antibody, for example, in a concentration of 0.1% to 99%, and the antibody may be administered to a subject at a dose of 0.05 to 2 mg per day. The predetermined dose may be administered once, or may also be administered at suitable intervals by divisional administration of two, three, four, or more times per day.

The present invention includes a therapeutic agent for canine atopic dermatitis, comprising, as an active ingredient, an anti-canine TARC monoclonal antibody, and further, a method for treating canine atopic dermatitis, comprising administering the anti-canine TARC monoclonal antibody to a dog. Moreover, a therapeutic agent molecularly targeting canine TARC is also included in the scope of the present invention.

EXAMPLES

The present invention will be described in the following Examples. However, these examples are not intended to limit the scope of the present invention.

Example 1 Production of Recombinant Canine TARC Protein Used as Antigen, Using *Escherichia coli*

Plasmid DNA comprising a full-length protein translation region of canine TARC, which had been reported by Maeda et al. (J. Vet. Med. Sci. 63(9): 1035-1038, 2001) in a study paper, was used as a template, and a DNA fragment encoding a canine TARC protein was prepared according to a PCR method. The DNA fragment was linked with an *Escherichia coli* expression vector pGEX4T-1 (Amersham Bioscience). *Escherichia coli* were transformed with the expression vector, and *Escherichia coli* clones comprising a canine TARC gene were then selected. Thereafter, plasmid DNA was purified. The *Escherichia coli* BL21 strain (TaKaRa) was transformed with the thus obtained plasmid DNA. The transformed *Escherichia coli* was cultured in an LB medium (supplemented with 50 µg/mL ampicillin), and 100 mM IPTG was then added to the culture medium to induce expression. Thereafter the *Escherichia coli* were further cultured at 37° C. for 3 hours. Subsequently, the culture medium was transferred into a centrifuge tube, and was then centrifuged at 4° C. at 6,000 rpm for 10 minutes, so as to collect cells.

The supernatant was removed, and the precipitate was then suspended in a sonification buffer that had been cooled on ice (50 mM Tris-HCl, 50 mM NaCl, 1 mM EDTA, and 1 mM DTT; pH 8.0). The suspension was subjected to an ultrasonic treatment to disrupt *Escherichia coli*. Cooled 10% Triton X-100 was added to the reaction solution to a final concentration of 1%, and the obtained mixture was then centrifuged at 4° C. at 18,000 rpm for 30 minutes. The supernatant was subjected to an FPLC Pharmacia FPLC System, in which a Glutathione Sepharose 4B column (Amersham Bioscience) and a gel filtration column Superrose12HR10/30 (Amersham Bioscience) were used, so that a canine TARC protein to be used as an antigen was purified.

Example 2 Production and Selection of Hybridomas

The purified canine TARC obtained in Example 1 was dissolved in purified water to a concentration of 100 µg/100 µL, and the obtained solution was then administered into the abdominal cavity of a BALB/c mouse every two weeks for immunization. In the first and second immunizations, an emulsion comprising canine TARC and the equal volume of a Freund's complete adjuvant was administered. On the 3rd day after the final immunization, the spleen was excised, B lymphocytes were then separated, and the B lymphocytes were then fused with mouse myeloma cells according to the method of Koehler and Milstein et al. (Koehler, G., et al. Nature vol. 256, 495-497, 1975). Thereafter, the cells were cultured in a HAT medium, so as to select fused cells.

Subsequently, from the selected cells, hybridomas generating an anti-canine TARC antibody having high specificity were selected and obtained by a combination of solid-phase ELISA and Western blotting after the reduction treatment.

Specifically, a culture medium of hybridomas was directly reacted with a solid-phase antigen (canine TARC), and thereafter, hybridomas, which exhibited positive in ordinary solid-phase ELISA for confirming reactivity and also exhibited positive in Western blotting after the reduction treatment, were selected.

100 µl of the purified canine TARC (10 µg/ml 0.1 M NaHCO$_3$) obtained in Example 1 was added to a 96-well immunoplate (Nunc), and it was then immobilized at room temperature overnight. After completion of the immobilization of the canine TARC, each well was blocked with 100 µL of 1% BSA-PBS at 37° C. for 1 hour. The well was washed with PBS supplemented with 0.05% Tween 20 (a washing buffer) three times, and 50 µl each of the culture medium of hybridomas was added to the well, on which canine TARC had been immobilized, followed by performing incubation at 37° C. for 1 hour. After completion of the reaction for 1 hour, each well was washed with a washing buffer 5 times. In order to detect a canine TARC-binding antibody (mouse IgG), a peroxidase (POD)-labeled goat anti-mouse IgG (γ) polyclonal antibody (Zymet) was 2000 times diluted with 1% BSA-PBS, and 50 µL of the diluted solution was then added to each well of a 96-well immunoplate, and the obtained mixture was then reacted at 37° C. for 1 hour. Thereafter, each well was washed with a washing buffer 5 times, and 50 µL of enzyme substrate solution (ABTS solution) was then added to each well, followed by performing a reaction at 37° C. for 10 minutes. The enzyme reaction was terminated by adding 50 µL of 0.32% sodium fluoride solution to each well. The absorbance at 414 nm of each well was measured using an immunoreader (BioRad). Solid-phase ELISA was performed on individual hybridomas to select them. Cloning was performed on the obtained hybridomas three times, so that 8 hybridoma clones were established.

Example 3 Examination of Anti-Canine TARC Monoclonal Antibody CT-1

Among the 8 hybridoma clones, monoclonal antibodies generated from CT-1, CT-2, CT-F and CT-G (which are referred to as a CT-1 antibody, a CT-2 antibody, a CT-F antibody, and a CT-G antibody, respectively) were examined by ELISA, in terms of the reactivity of these antibodies with canine TARC.

The above-described monoclonal antibodies were each immobilized on wells of a microplate, which had been blocked using Block Ace at 37° C. for 1.5 hours. Thereafter, the recombinant canine TARC protein produced in Example 1 was added thereto and was then reacted therewith at 37° C. for 1.5 hours, so that the protein was allowed to bind to the antibody. The plate was washed, and a rabbit anti-canine TARC polyclonal antibody was added as a primary antibody to the plate. The obtained mixture was reacted at 37° C. for 1.5 hours. Thereafter, the plate was further washed, and HRP-labeled anti-rabbit IgG was added as a secondary antibody to the plate. The obtained mixture was reacted at 37° C. for 1.5 hours. A substrate was added, and the color development in each well was then measured.

FIG. 1 shows the reactivity of each monoclonal antibody. FIG. 1 shows both the results obtained in the case of adding TARC and the results obtained in the case of not adding TARC.

Figure 2:
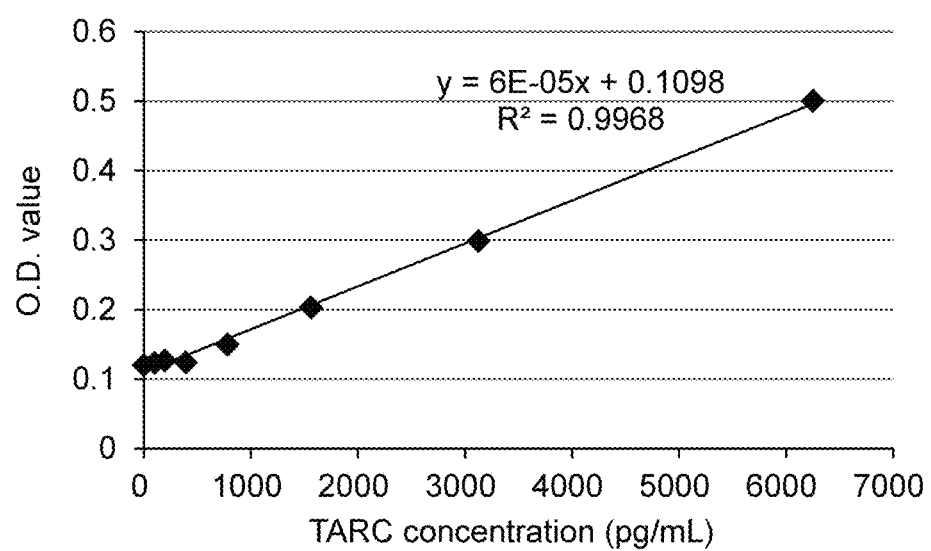
FIG. 2 is a view showing the reactivity obtained when the concentration of a TARC protein is changed using a CT-1 antibody.

The results shown in FIG. 1 demonstrate that the reactivity of the CT-F antibody and the CT-G antibody is high. However, the linearity obtained when the concentration of the added TARC protein was changed was more excellent in the CT-1 antibody than the aforementioned antibodies. FIG. 2 shows reactivity obtained when the concentration of the TARC protein was changed using the CT-1 antibody. As shown in FIG. 2, $R^2=0.9968$, and the linearity was favorable.

Example 4 Measurement of TARC Protein in Serum of Canine Subjects, Using CT-1 Antibody Blood was collected from each of 9 healthy dogs, 9 dogs affected with atopic dermatitis, and 9 dogs artificially sensitized with allergen, and thereafter, the concentration of a TARC protein in the serum was measured. Sensitization was carried out by mixing Derf2 allergen with aluminum hydroxide gel, and then subcutaneously administering the obtained mixture to the dogs 2 or 3 times. Thereafter, the establishment of sensitization was confirmed based on an increase in anti-derf2 IgE in the serum.

Figure 3:
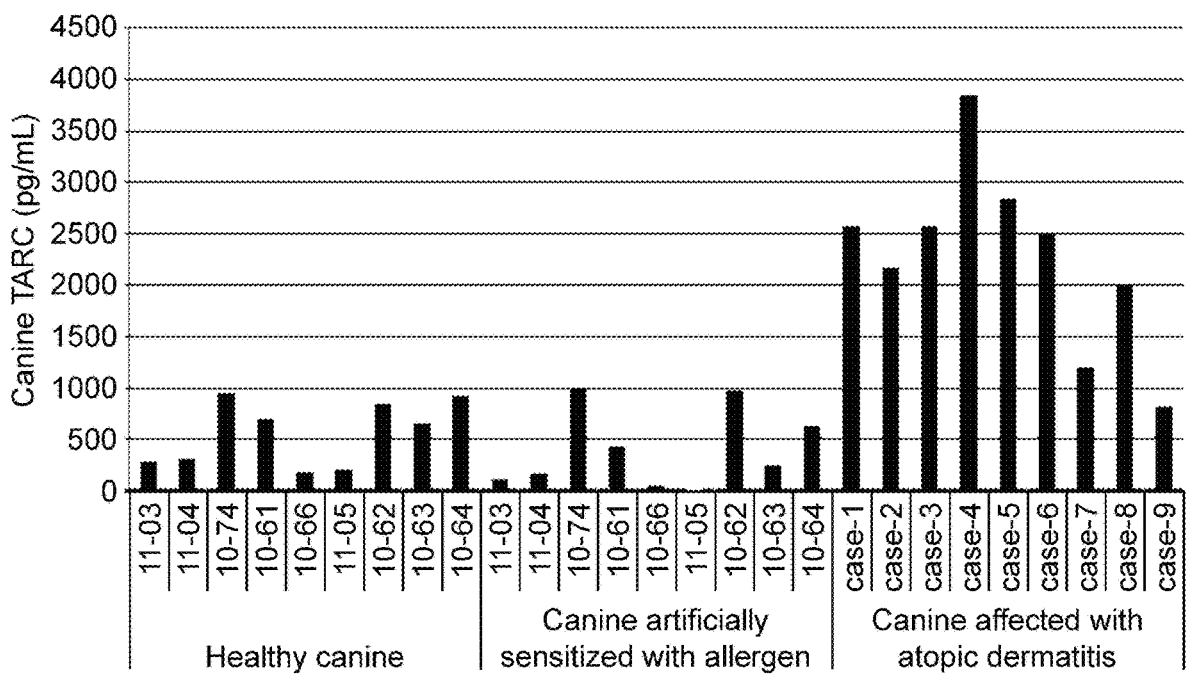
FIG. 3 is a view showing the results obtained by measuring canine TARC contained in the serum of healthy canine subjects and canine subjects affected with atopic dermatitis, using a CT-1 antibody.

The results are shown in FIG. 3. The results of FIG. 3 demonstrate that canine atopic dermatitis can be detected with high sensitivity, when the CT-1 antibody is used.

Example 5 Determination of Nucleotide Sequence of Variable Region of CT-1 Antibody DNA encoding the variable region of a CT-1 antibody was isolated from hybridomas generating the CT-1 antibody, and the nucleotide sequence thereof was then determined.

Specifically, total RNA was prepared from hybridomas, and using the total RNA as a template, and also using SMARTer (trademark) RACE cDNA Amplification Kit (TaKaRa Code Z4923N) and primers specific to a rat antibody (IgG) H chain (heavy chain) constant region, an RT reaction was carried out. Using the obtained cDNA as a template, and also using primers specific to the H chain constant region, a RACE PCR reaction was carried out. The obtained PCR product was purified, and was then cloned into a plasmid vector. Thereafter, 48 clones, which were randomly picked up, were subjected to a nucleotide sequence analysis. Likewise, using total RNA prepared from hybridomas as a template, the analysis was carried out also on the L chain (light chain).

The following primers were used.
H-RT1: TCCAKAGTTCCA (SEQ ID NO: 5)
H-PCR-NA: GGGAARTARCCCTTGACCAGGCA (SEQ ID NO: 6)
H-PCR-N2: GGGAARTAGCCTTTGACAAGGCA (SEQ ID NO: 7)
L-RT1: GCTGTCCTGATC (SEQ ID NO: 8)
L-PCR: CACTGCCATCAATCTTCCACTTGACA (SEQ ID NO: 9)

The H-PCR-N1 primer was mixed with the H-PCR-N2 primer at a ratio of 1:1, and the obtained mixture was used as an H-PCR primer.

The nucleotide sequence of the heavy chain variable region is shown in SEQ ID NO: 1, and the nucleotide sequence of the light chain (κ chain) variable region is shown in SEQ ID NO: 3. In addition, the amino acid sequence of the heavy chain variable region is shown in SEQ ID NO: 2, and the amino acid sequence of the κ chain variable region is shown in SEQ ID NO: 4.

Example 6 Production of Recombinant CT-1 Monoclonal Antibody

A gene having a NotI enzyme site added to the 3'-terminal side of a canine immunoglobulin H chain constant region was amplified using primers (1 (SEQ ID NO: 10) and 2 (SEQ ID NO: 11)) (FIG. 4), employing KOD-Plus (Toyobo Co., Ltd.), in accordance with protocols included with the product (IgG-C). Similarly, a gene having a MluI gene added to the 3'-terminal side of a canine immunoglobulin L chain constant region was amplified using primers (3 (SEQ ID NO: 12) and 4 (SEQ ID NO: 13)) (FIG. 4) (IgG-kappa).

By the same method as described above, the H chain V region of the CT-1 monoclonal antibody was amplified using primers (5 (SEQ ID NO: 14) and 6 (SEQ ID NO: 15)) (FIG. 4) (CT1-mouse VH), so that it had a SalI enzyme site at the 5'-terminus thereof and a sequence partially overlapped with the sequence on the 5'-terminal side of IgG-C at the 3'-terminus thereof. A mixture of this CT1-mouse VH and the aforementioned IgG-C was used as a template, and overlap PCR was carried out using primers (2 (SEQ ID NO: 11) and 5 (SEQ ID NO: 14)) (FIG. 4), so that the mouse immunoglobulin H chain variable region was allowed to bind to the canine immunoglobulin H chain constant region, thereby obtaining a chimeric gene encoding the H chain of the CT-1 monoclonal antibody (CT1-mouse VH-canine CH).

Likewise, the L chain V region of the CT-1 monoclonal antibody was amplified using primers (7 (SEQ ID NO: 16) and 8 (SEQ ID NO: 17)) (FIG. 4) (CT1-mouse VL), so that it had a XhoI enzyme site at the 5'-terminus thereof and a sequence partially overlapped with the sequence at the 5'-terminus of IgG-kappa on the 3'-terminal side thereof. A mixture of this CT1-mouse VL and the aforementioned IgG-kappa was used as a template, and overlap PCR was carried out using primers (4 and 7) (FIG. 4), so that the mouse immunoglobulin L chain variable region was allowed to bind to the canine immunoglobulin L chain constant region, thereby obtaining a chimeric gene encoding the L chain of the CT-1 monoclonal antibody (CT1-mouse VL-canine CL).

Figure 5:
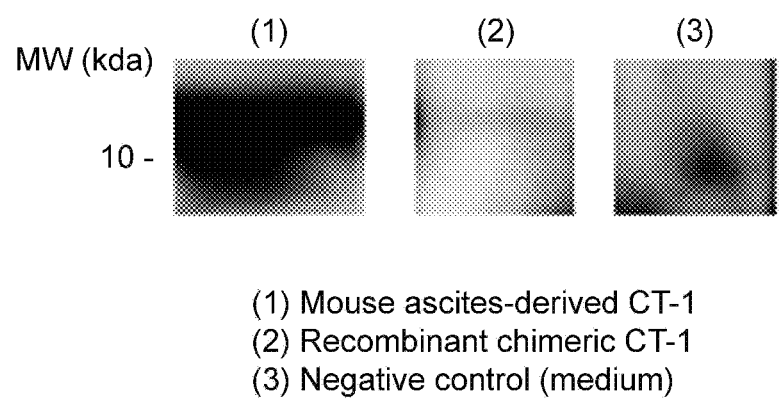
FIG. 5 is a view showing the results obtained by confirming the reactivity of a recombinant anti-canine TARC monoclonal antibody by Western blotting.

The CT1-mouse VH-canine CH gene and the CT1-mouse VL-canine CL gene were each subcloned into pIRES Vector (Clontech) by utilizing the restriction enzyme sequence added to each gene, so as to produce a chimeric antibody expression plasmid pIRES-chimeric CT-1. This pIRES-chimeric CT-1 was introduced into HEK293 cells, using Lipofectamine 200 (Invitrogen), and a chimeric anti-CT-1 monoclonal antibody was then obtained from the culture supernatant. The results are shown in FIG. 5. FIG. 5(2) shows a recombinant chimeric CT-1 antibody.

Example 7 Production of Anti-Canine TARC Antibodies, R1 Antibody, R5 Antibody, R7 Antibody and CT-3 Antibody An R1 antibody, an R5 antibody, an R7 antibody and a CT-3 antibody were obtained by the same method as applied in the case of the CT-3 antibody, and were then sequenced.

The nucleotide sequence of DNA encoding the heavy chain variable region of an R1 antibody consists of the nucleotide sequence shown in SEQ ID NO: 18, and the amino acid sequence of the heavy chain variable region consists of the amino acid sequence shown in SEQ ID NO: 19. In addition, the nucleotide sequence of DNA encoding the light chain variable region of an R1 antibody consists of the nucleotide sequence shown in SEQ ID NO: 20, and the amino acid sequence of the light chain variable region consists of the amino acid sequence shown in SEQ ID NO: 21.

The nucleotide sequence of DNA encoding the heavy chain variable region of an R5 antibody consists of the nucleotide sequence shown in SEQ ID NO: 22, and the amino acid sequence of the heavy chain variable region consists of the amino acid sequence shown in SEQ ID NO: 23. In addition, the nucleotide sequence of DNA encoding the light chain variable region of an R5 antibody consists of the nucleotide sequence shown in SEQ ID NO: 24, and the amino acid sequence of the light chain variable region consists of the amino acid sequence shown in SEQ ID NO: 25.

The nucleotide sequence of DNA encoding the heavy chain variable region of an R7 antibody consists of the nucleotide sequence shown in SEQ ID NO: 26, and the amino acid sequence of the heavy chain variable region consists of the amino acid sequence shown in SEQ ID NO: 27. In addition, the nucleotide sequence of DNA encoding the light chain variable region of an R7 antibody consists of the nucleotide sequence shown in SEQ ID NO: 28, and the amino acid sequence of the light chain variable region consists of the amino acid sequence shown in SEQ ID NO: 29.

The nucleotide sequence of DNA encoding the heavy chain variable region of a CT-3 antibody consists of the nucleotide sequence shown in SEQ ID NO: 30, and the amino acid sequence of the heavy chain variable region consists of the amino acid sequence shown in SEQ ID NO: 31. In addition, the nucleotide sequence of DNA encoding the light chain variable region of a CT-3 antibody consists of the nucleotide sequence shown in SEQ ID NO: 32, and the amino acid sequence of the light chain variable region consists of the amino acid sequence shown in SEQ ID NO: 33.

INDUSTRIAL APPLICABILITY

The anti-canine TARC antibody of the present invention can be used in the diagnosis and treatment of canine atopic dermatitis.

All publications, patents and patent applications cited in the present description are incorporated herein by reference in their entirety.

SEQUENCE LISTING FREE TEXT

SEQ ID NOS: 5 to 17 Primers

The invention claimed is:

1. An anti-canine Thymus Activation-Regulated Chemokine (TARC) monoclonal antibody binding to canine TARC, comprising:
   (i) a heavy chain variable region consisting of the amino acid sequence shown in any one of SEQ ID NO: 2, 19, 23, 27 and 31, and
   (ii) a light chain variable region consisting of the amino acid sequence shown in any one of SEQ ID NO: 4, 21, 25, 29 and 33,
   (iii) a heavy chain variable region encoded by DNA consisting of the nucleotide sequence shown in any one of SEQ ID NO: 1, 18, 22, 26 and 30, and
   (iv) a light chain variable region encoded by DNA consisting of the nucleotide sequence shown in any one of SEQ ID NO: 3, 20, 22, 26 and 30.

2. The anti-canine TARC monoclonal antibody according to claim 1, wherein the heavy chain constant region and the light chain constant region are the constant regions of a canine IgG antibody.

3. The anti-canine TARC monoclonal antibody binding to canine TARC according to claim 1, wherein the functional fragment is a peptide fragment selected from the group consisting of Fab, Fab', F(ab')$_2$, a disulfide bond Fv (dsFv), a dimerized V region (diabody), and a single chain Fv (scFv).

4. A polypeptide of any one of the following (i) and (ii):
   (i) A polypeptide that is the heavy chain variable region of an anti-canine TARC monoclonal antibody, the polypeptide consisting of the amino acid sequence shown in any one of SEQ ID NO: 2, 19, 23, 27 and 31; and
   (ii) A polypeptide that is the light chain variable region of an anti-canine TARC monoclonal antibody, the polypeptide consisting of the amino acid sequence shown in any one of SEQ ID NO: 4, 21, 25, 29 and 33.

5. A detection reagent for canine atopic dermatitis, comprising the anti-canine TARC monoclonal antibody binding to canine TARO according to claim 1, wherein said heavy chain variable region consists of the amino acid sequence of SEQ ID NO: 2 and said light chain variable region consist of the amino acid sequence of SEQ ID NO:4.

6. A method for detecting canine atopic dermatitis, which comprises measuring TARC in serum collected from a canine, by reacting the detecting reagent according to claim 5 with a sample.

* * * * *